United States Patent
Subbaroyan et al.

(10) Patent No.: US 12,226,634 B2
(45) Date of Patent: Feb. 18, 2025

(54) HIGH FREQUENCY STIMULATION FOR TREATING SENSORY AND/OR MOTOR DEFICITS IN PATIENTS WITH SPINAL CORD INJURIES AND/OR PERIPHERAL POLYNEUROPATHY, AND ASSOCIATED SYSTEMS AND METHODS

(71) Applicant: Nevro Corp., Redwood City, CA (US)

(72) Inventors: Jeyakumar Subbaroyan, Floral Park, NY (US); Kerry Bradley, Glendale, CA (US); Dongchul Lee, Agua Dulce, CA (US)

(73) Assignee: Nevro Corp., Redwood City, CA (US)

( * ) Notice: Subject to any disclaimer, the term of this patent is extended or adjusted under 35 U.S.C. 154(b) by 0 days.

(21) Appl. No.: 17/330,310

(22) Filed: May 25, 2021

(65) Prior Publication Data

US 2021/0275812 A1 Sep. 9, 2021

Related U.S. Application Data

(63) Continuation of application No. 16/937,463, filed on Jul. 23, 2020, now abandoned, which is a
(Continued)

(51) Int. Cl.
*A61N 1/36* (2006.01)
*A61N 1/05* (2006.01)
*A61N 1/372* (2006.01)

(52) U.S. Cl.
CPC ..... *A61N 1/36062* (2017.08); *A61N 1/36171* (2013.01); *A61N 1/0551* (2013.01);
(Continued)

(58) Field of Classification Search
CPC ...... A61B 5/0031; A61B 5/4094; A61N 1/00; A61N 1/02; A61N 1/36067;
(Continued)

(56) References Cited

U.S. PATENT DOCUMENTS 5,806,522 A 9/1998 Katims
6,721,603 B2 4/2004 Zabara et al.
(Continued)

FOREIGN PATENT DOCUMENTS

JP 2018500143 1/2018
JP 2013521979 5/2021
(Continued)

OTHER PUBLICATIONS

Seattle Pain Relief. "Seattle Pain Relief Now Helping Diabetic Neuropathy Patients Restore Sensation with Spinal Cord Stimulation." PRWeb</i>, Nov. 16, 2015, https://www.prweb.com/releases/diabetic-neuropathy/seattle-tacoma-wa/prweb13080906.htm (Year: 2015).*

(Continued)

*Primary Examiner* — David Hamaoui
*Assistant Examiner* — Adreanne A. Arnold
(74) *Attorney, Agent, or Firm* — Perkins Coie LLP (57) ABSTRACT

High frequency stimulation for treating sensory and/or motor deficits in patients with spinal cord injuries and/or peripheral polyneuropathy, and associated systems and methods. A representative method includes addressing the patient's somatosensory dysfunction and/or motor dysfunction, resulting from neuropathy and/or spinal cord injury, by directing an electrical therapy signal to the patient's spinal cord region, the therapy signal having a frequency in a frequency range from 1.5 kHz to 100 KHz.

25 Claims, 6 Drawing Sheets

Related U.S. Application Data continuation of application No. 15/874,504, filed on Jan. 18, 2018, now abandoned.

(60) Provisional application No. 62/588,185, filed on Nov. 17, 2017, provisional application No. 62/448,320, filed on Jan. 19, 2017.

(52) U.S. Cl.
CPC ...... *A61N 1/36139* (2013.01); *A61N 1/36157* (2013.01); *A61N 1/36175* (2013.01); *A61N 1/37217* (2013.01)

(58) Field of Classification Search
CPC ............ A61N 1/36096; A61N 1/36092; A61N 1/36071; A61N 1/0551; A61N 1/36062; A61N 1/36139; A61F 2007/0027; A61F 2007/0026; A61F 2007/0025; A61F 2007/0024

See application file for complete search history.

(56) References Cited

U.S. PATENT DOCUMENTS

| | | |
|---|---|---|
| 6,871,099 B1 | 3/2005 | Whitehurst et al. |
| 7,162,304 B1 | 1/2007 | Bradley |
| 7,206,632 B2 | 4/2007 | King |
| 8,355,797 B2 | 1/2013 | Caparso |
| 8,569,935 B1 | 10/2013 | Kosierkiewicz |
| 8,712,533 B2 | 4/2014 | Alataris et al. |
| 8,768,472 B2 | 7/2014 | Fang |
| 8,903,501 B2 | 12/2014 | Perryman |
| 8,918,190 B2 | 12/2014 | Libbus et al. |
| 8,954,153 B2 | 2/2015 | Boggs, II |
| 9,002,477 B2 | 4/2015 | Burnett |
| 9,295,841 B2 | 3/2016 | Fang et al. |
| 9,327,121 B2 * | 5/2016 | Thacker ............ A61N 1/36171 |
| 9,387,338 B2 | 7/2016 | Burnett |
| 9,452,286 B2 | 9/2016 | Cowan et al. |
| 9,486,632 B2 | 11/2016 | Saab |
| 9,486,633 B2 | 11/2016 | Kramer et al. |
| 9,533,149 B2 | 1/2017 | Lee et al. |
| 9,561,371 B2 | 2/2017 | Elborno |
| 9,630,011 B2 | 4/2017 | Lipani |
| 9,757,584 B2 | 9/2017 | Burnett et al. |
| 9,782,589 B2 | 10/2017 | Oron et al. |
| 9,789,313 B2 | 10/2017 | Lipani |
| 9,833,614 B1 | 12/2017 | Gliner |
| 9,861,547 B2 | 1/2018 | Crunick et al. |
| 9,884,189 B2 | 2/2018 | Boggs, II |
| 9,895,530 B2 | 2/2018 | Boggs, II |
| 9,895,539 B1 | 2/2018 | Heit |
| 9,950,164 B2 | 4/2018 | Lipani |
| 10,143,850 B2 | 12/2018 | Cowan et al. |
| 10,307,585 B2 | 1/2019 | Boggs et al. |
| 10,493,275 B2 | 2/2019 | Alataris |
| 10,232,180 B2 | 3/2019 | Kramer et al. |
| 10,238,872 B2 | 3/2019 | Pivonka et al. |
| 10,328,256 B1 | 6/2019 | Gliner |
| 10,342,977 B2 | 7/2019 | Raghunathan |
| 10,369,366 B2 | 8/2019 | Oron et al. |
| 10,426,959 B2 | 10/2019 | Boggs, II |
| 10,583,284 B2 | 3/2020 | Peters et al. |
| 10,668,285 B2 | 6/2020 | Boggs, II |
| 10,799,701 B2 | 10/2020 | Lee |
| 11,534,611 B2 | 12/2022 | Baldoni |
| 11,986,657 B2 | 5/2024 | Lee et al. |
| 2003/0018367 A1 | 1/2003 | DiLorenzo |
| 2003/0055464 A1 | 3/2003 | Darvish et al. |
| 2004/0015204 A1 | 1/2004 | Whitehurst |
| 2004/0039425 A1 | 2/2004 | Greenwood-Van Meerveld |
| 2005/0240241 A1 | 10/2005 | Yun et al. |
| 2008/0033511 A1 | 2/2008 | Dobak et al. |
| 2008/0077192 A1 | 3/2008 | Harry et al. |
| 2009/0076565 A1 | 3/2009 | Surwit |
| 2010/0274314 A1 | 10/2010 | Alataris |
| 2010/0274326 A1 | 10/2010 | Chitre et al. |
| 2012/0303098 A1 | 11/2012 | Perryman |
| 2013/0116754 A1 | 5/2013 | Sharma et al. |
| 2013/0204324 A1 | 8/2013 | Thacker et al. |
| 2013/0274846 A1 | 10/2013 | Lad et al. |
| 2014/0276549 A1 | 9/2014 | Osorio |
| 2014/0316484 A1 | 10/2014 | Edgerton et al. |
| 2015/0073510 A1 | 3/2015 | Perryman |
| 2016/0030408 A1 | 2/2016 | Levin |
| 2016/0082252 A1 | 3/2016 | Hershey et al. |
| 2016/0121109 A1 | 5/2016 | Edgerton |
| 2016/0175594 A1 | 6/2016 | Min et al. |
| 2016/0177298 A1 | 6/2016 | Green |
| 2016/0213918 A1 | 7/2016 | Howard et al. |
| 2016/0256863 A1 | 9/2016 | Butera et al. |
| 2017/0036023 A1 | 2/2017 | Parker |
| 2017/0095667 A1 | 4/2017 | Yakovlev |
| 2017/0274212 A1 | 9/2017 | Kramer et al. |
| 2017/0354831 A1 | 12/2017 | Burnett et al. |
| 2018/0085580 A1 | 3/2018 | Perez et al. |
| 2018/0256906 A1 | 9/2018 | Pivonka et al. |
| 2018/0272132 A1 | 9/2018 | Subbaroyan et al. |
| 2018/0318585 A1 | 11/2018 | Pfeifer |
| 2018/0345020 A1 | 12/2018 | Ironi et al. |
| 2018/0361154 A1 | 12/2018 | Levin |
| 2019/0001139 A1 | 1/2019 | Mishra et al. |
| 2019/0046795 A1 | 2/2019 | Cakmak |
| 2019/0151652 A1 | 5/2019 | Boggs, II |
| 2019/0232062 A1 | 8/2019 | Falowski |
| 2019/0269913 A1 | 9/2019 | Pivonka et al. |
| 2019/0321641 A1 | 10/2019 | Baldoni et al. |
| 2019/0336776 A1 | 11/2019 | Cowan et al. |
| 2019/0351235 A1 | 11/2019 | Leuthardt et al. |
| 2019/0374776 A1 | 12/2019 | Mishra et al. |
| 2020/0030606 A1 | 1/2020 | Boggs, II |
| 2020/0046973 A1 | 2/2020 | Simon et al. |
| 2020/0046981 A1 | 2/2020 | Kramer et al. |
| 2020/0108251 A1 | 4/2020 | Raghunathan |
| 2020/0139138 A1 * | 5/2020 | Sit ........................ H04B 5/0031 |
| 2020/0254255 A1 | 8/2020 | Lee |
| 2020/0324113 A1 * | 10/2020 | Fisher ................... A61B 5/486 |
| 2020/0353253 A1 | 11/2020 | Subbaroyan |
| 2021/0085981 A1 | 3/2021 | Lee |
| 2021/0275812 A1 | 9/2021 | Subbaroyan et al. |
| 2021/0330981 A1 | 10/2021 | Mishra et al. |
| 2023/0248973 A1 | 8/2023 | Subbaroyan et al. |

FOREIGN PATENT DOCUMENTS

| | | |
|---|---|---|
| KR | 10-2021-0050493 | 6/2013 |
| WO | WO-2013036880 | 3/2013 |
| WO | WO-2013116368 | 8/2013 |
| WO | WO-2014146082 | 9/2014 |
| WO | WO-2017044904 | 3/2017 |
| WO | WO-2017142948 | 8/2017 |
| WO | WO-2017146658 | 8/2017 |
| WO | WO-2018125538 | 7/2018 |
| WO | WO-2020051484 | 3/2020 |

OTHER PUBLICATIONS

Al-Kaisy et al., "The Use of 10-Kilohertz Spinal Cord Stimulation in Cohort of Patients with Chronic Neuropathic Limb Pain Refractory to Medical Management," Neuromodulation: Technology at the Neural Interface, Feb. 2014, 7 pages.

Tesfaye et al., "Electrical Spinal-Cord Stimulation for Painful Diabetic Peripheral Neuropathy," The Lancet, vol. 348, Dec. 1996, 4 pages.

Van Beek et al., "Spinal Cord Stimulation in Experimental Chronic Painful Diabetic Polyneuropathy: Delayed Effect of High-Frequency Stimulation," European Journal of Pain, Oct. 2016, 9 pages.

Seattle Pain Relief Now Helping Diabetic Neuropathy Patients Restore Sensation with Spinal Cord Stimulation, PRWeb Online Visibility from Vocus, https://www.prweb.com/releases/diabetic-neuopathy/seattle-tacoma-wa/prweb13080906.htm, 2015, 2 pages.

(56) References Cited

OTHER PUBLICATIONS

Ahmed et al., "Effects of Spinal Cord Stimulation on Pain Thresholds and Sensory Perceptions in Chronic Pain Patients," Neuromodulation. 2015;18(5):6 pages.
Daousi C et al., "Electrical spinal cord stimulation in the long-term treatment of chronic painful diabetic neuropathy" Diabet Med. 2005;22(4):6 pages.
De Vos et al., "Burst spinal cord stimulation evaluated in patients with failed back surgery syndrome and painful diabetic neuropathy" Neuromodulation. 2014;17(2): 8 pages.
De Vos et al., Effect and safety of spinal cord stimulation for treatment of chronic pain caused by diabetic neuropathy. J Diabetes Complications. 2009;23(1): 6 pages.
De Vos et al., "Spinal cord stimulation in patients with painful diabetic neuropathy: a multicentre randomized clinical trial," Pain. 2014;155(11):.6 pages.
Duarte et al., "Quality of life increases in patients with painful diabetic neuropathy following treatment with spinal cord stimulation" Qual Life Res. 2016;25(7):7 pages.
Eisenberg et al., "Quantitative Sensory Testing for Spinal Cord Stimulation in Patients With Chronic Neuropathic Pain. Pain Practice" 2006;6(3):5 pages.
Eldabe et al. "Retrospective Case Series on the Treatment of Painful Diabetic Peripheral Neuropathy With Dorsal Root Ganglion Stimulation." Neuromodulation. 2018;21(8): 6 pages.
Koetsier et al., "Effectiveness of dorsal root ganglion stimulation and dorsal col. spinal cord stimulation in a model of experimental painful diabetic polyneuropathy," CNS Neurosci Ther. 2019;25(3): 8 pages.
Koetsier et al., "Mechanism of dorsal root ganglion stimulation for pain relief in painful diabetic polyneuropathy is not dependent on GABA release in the dorsal horn of the spinal cord" CNS Neurosci Ther. 2020;26(1): 8 pages.
Kumar et al., "Spinal cord stimulation for chronic pain in peripheral neuropathy" Surg Neurol. 1996;46(4):7 pages.
Pluijms et al. "Increased contact heat evoked potential stimulation latencies in responders to spinal cord stimulation for painful diabetic polyneuropathy," Neuromodulation. 2015;18(2) 7 pages.
Pluijms et al., "Pain relief and quality-of-life improvement after spinal cord stimulation in painful diabetic polyneuropathy: a pilot study" British Journal of Anaesthesia. 2012;109(4):7 pages.
Pluijms et al., "The effect of spinal cord stimulation frequency in experimental painful diabetic polyneuropathy" Eur J Pain. 2013;17(9):9 pages.
Slangen et al., "Spinal cord stimulation and pain relief in painful diabetic peripheral neuropathy: a prospective two-center randomized controlled trial" Diabetes Care. 2014;37(11): 9 pages.
Van Beek et al. "Sustained Treatment Effect of Spinal Cord Stimulation in Painful Diabetic Peripheral Neuropathy: 24-Month Follow-up of a Prospective Two-Center Randomized Controlled Trial. Diabetes Care" 2015;38(9):3 pages.
Van Beek et al., "Long-Term Spinal Cord Stimulation Alleviates Mechanical Hypersensitivity and Increases Peripheral Cutaneous Blood Perfusion in Experimental Painful Diabetic Polyneuropathy" Neuromodulation. 2018;21(5):8 pages.
Van Beek et al., "Severity of Neuropathy Is Associated With Long-term Spinal Cord Stimulation Outcome in Painful Diabetic Peripheral Neuropathy: Five-Year Follow-up of a Prospective Two-Center Clinical Trial" Diabetes Care. 2018;41(1): 7 pages.
Cata et al., "Spinal cord stimulation relieves chemotherapy-induced pain: A Clinical Case Report," Journal of Pain and Symptom Management-10.1016/j.jpainsymman, vol. 27, No. 1, Jan. 2004, 7 pages.
Cision PRWeb, "Seattle Pain Relief Now Offering Groundbreaking Treatments for Diabetic and Peripheral Neuropathy," http://www.prweb.com/releases/seattle-pain-center/diabeticneuropathydoctor/prweb12492970.htm Jul. 25, 2022, 3 pages.
Lachance et al., "Stimulation-induced ectopicity and propagation windows in model damaged axons," J. Comput Neurosci, 2014, 9 pages.
McDonnell et al., "Treatment of pain secondary to diabetic peripheral neuropathy (DPN) wit the precisions spinal cord stimulation (SCS) system: a case series," European Journal of Pain 11(S1), 2007, 1 page.
National Institute of Neurological Disorders and Stroke (NINDS), "Paresthesia," https://www.ninds.gov/Disorders/All-Disorders/Paresthesia-Information-Page#disorders-r3>, 2014.
Seattle Pain Relief Video: "What is a Spinal Cord Stimulator," https://www.painmanagement-seattle.com/spinal-cord-stimulator.html 2016, 5 pages.
YouTube Video: Spinal Cord Stimulator Implants Help Diabetic Peripheral Neuropathy (602) 507-6550, https://www.youtube.com/watch?v=EYao-SfPOwo, Jul. 23, 2012, 3 pages.
Zhu et al., "Changes in functional properties of A-type but not C-type sensory neurons in vivo in a rat model of peripheral neuropathy," Journal of Pain Research, Dovepress, 2012, 18 pages.
Zhu et al., "Early Demyelination of Primary A-Fibers Induces a Rapid-Onset of Neuropathic Pain in Rat," Neuroscience 200, 2012, 13 pages.
Zhu et al., "Excitability of Aβ sensory neurons is altered in an animal model of peripheral neuropathy," BMC Neuroscience, 13:15, 2012, 15 pages.
Mayo Clinic, "Diabetic Neuropathy," https://www.mayoclinic.org/diseases-conditions/diabetic-neuropathy/symptoms-causes/syc-20371580, 1998, 5 pages.
Slangen et al., "Sustained effect of spinal cord" stimulation on pain and quality of life in painful diabetic peripheral neuropathy British Journal of Anaesthesla, 2013;111(6):1030-1031, 2 pages.
Karamian et al., "The role of electrical stimulation for rehabilitation and regeneration after spinal cord injury," Journal of Orthopaedics and Traumatology, Jan. 6, 2022, 18 pages.

* cited by examiner

| | Demography | Diagnoses/ Etiology | Time since Injury | Location of Injury | Medical History | Pre-Treatment Symptoms | Pre-Treatment Pain Location | Pre-Treatment VAS | Lead Location | Best Program | Post-Treatment Symptoms | Post-Treatment VAS | Post-Treatment Comments |
|---|---|---|---|---|---|---|---|---|---|---|---|---|---|
| Patient 1 | 62, F | SCI injury- Fell off ski lift | 33 years | T8 | Wheelchair bound; ITP for spasticity, multilevel thoracic laminectomy w/SC detethering | Paraplegia, dystonia, spasms ("dancing legs"), able to sit for only 10-15 mins | Low back, chest wall | Low back: 8 upper back: 9, right UL: 8 and bilateral leg: 9 | T8-T11 | Cascade on top lead | Spasms stopped; Able to sit for several hours | Low back: 3 (perc trial); Upper back, bilateral leg: zero, R UL: 2 | Perc leads in gutter, 2nd trial w paddle leads; Pain relief in upper back, leg and right UL with MA program (Lower C6: 1-3 and Lower T5: 9-11) w/20s on for each area |
| Patient 2 | 32, F | Cervical SCI w incomplete quadriplegia; dislocated ribs in car accident | | | Multi-level cervical fusion; Blocks for dislocated ribs | Thoracic pain; uses crutch/cane; Spasticity | Upper back | 7 | C1-T10 | Mid T2 | improvement in movement ("tone", walk smoothly), functional capacity in paralyzed leg, reduction in rib pain; Improvement in spasticity; Transition from seated to standing positions that | 2 | |
| Patient 3 | | Migraine; Partial SCI w "significant damage at T9/10" | 8 years | | | Paraplegic | Migraine; Low back pain | 8 | | C3, 1.4 mA (Duty cycling) | Mild sensation in legs (slight itching); pin prick sensation which went away when stim was off; Flex both ankles in dorsi- and plantar-flexion; stand | 5 and at last follow-up (Trial) | HF10 trialed for head pain and migraine; Failed other neuromod therapies; Migraine and LBP under control |
| Patient 4 | | | | | | pain in foot for 22 years; could not feel pin prick at foot; no Babinski | Foot | 9.9 | Top of T8 to top of T12 | Bipole between contacts 14 and 15 | Reduced pain in foot; could feel pin prick at foot (maintained through 6 month post-implant visit); had normal Babinski reflex | 6.9 | |
| Patient 5 | | Small fiber neuropathy | | | | No sensation in feet | n/a | | | | Sensation in feet | | |

| Sex | Age | Patient Diagnosis | Medication Adjustment During Follow-up | Sensation Level Relative to Baseline |
|---|---|---|---|---|
| M | 66 | Idiopathic | reduced | no change |
| M | 63 | Idiopathic | reduced | improved, reported 25% |
| M | 34 | DPN | reduced | not reported |
| F | 57 | DPN | Completely off Medication | improved, reported 60% |
| M | 70 | DPN | NA (no meds at baseline) | improved |
| F | 70 | CIPD | no change* | NA |

* medications were initially reduced, later adjusted up due to new pain in the upper body

HIGH FREQUENCY STIMULATION FOR TREATING SENSORY AND/OR MOTOR DEFICITS IN PATIENTS WITH SPINAL CORD INJURIES AND/OR PERIPHERAL POLYNEUROPATHY, AND ASSOCIATED SYSTEMS AND METHODS

CROSS-REFERENCE TO RELATED APPLICATIONS

The present application is a continuation of U.S. Non-provisional patent application Ser. No. 16/937,463, filed Jul. 23, 2020, which is a continuation of U.S. Non-Provisional patent application Ser. No. 15/874,504, filed Jan. 18, 2018, and claims priority to the following US Provisional Patent Applications: U.S. Provisional Patent Application 62/448,320, filed on Jan. 19, 2017; and US Provisional Patent Application 62/588,185, filed on Nov. 17, 2017; both of which are incorporated herein by reference in their entireties.

TECHNICAL FIELD

The present disclosure is directed generally to high frequency electrical stimulation for treating sensory and/or motor deficits in patients with spinal cord injuries and/or peripheral polyneuropathy, and associated systems and methods.

BACKGROUND

An estimated 20 million people in the United States have some form of peripheral neuropathy, a condition that develops as a result of damage to the peripheral nervous system ("PNS"). The PNS is a vast communications network that connects the central nervous system ("CNS") to the limbs and organs, essentially serving as a communication relay going back and forth between the brain and spinal cord with the rest of the body. Damage to the PNS interferes with this communication pathway, and symptoms can range from numbness or tingling, to pricking sensations or muscle weakness. Peripheral neuropathy has been conventionally treated with medication, injection therapy, physical therapy, surgery, and light. More recently, diabetic peripheral neuropathy has been treated by applying a surface electrical stimulation at a specified frequency to the muscles and nerves. Most treatments are designed to treat the underlying cause of the neuropathy, but in many cases, the cause of the neuropathy is unknown or, even if the cause has been identified, a specific treatment may not exist. Accordingly, there is a need for systems and methods for treating peripheral neuropathy.

DETAILED DESCRIPTION

1.0 Introduction

The present technology is directed generally to systems and methods for treating peripheral neuropathy, peripheral polyneuropathy (PPN), painful diabetic neuropathy (PDN), dysesthesia, sensory deficits, motor deficits, and/or spinal cord injury using high frequency electrical stimulation. In particular, the systems and methods of the present technology may at least partially restore sensory loss in patients suffering from peripheral neuropathy and/or other indications. In one embodiment, the present technology includes improving the patient's somatosensory function by delivering an electrical signal, having a frequency of from 1.5 kHz to 100 kHz to the patient's spinal cord via at least one implantable signal delivery device, and wherein the electrical signal has a frequency of from 1.5 kHz to 100 KHz.

Definitions of selected terms are provided under heading 1.0 ("Definitions"). General aspects of the anatomical and physiological environment in which the disclosed technology operates are described below under heading 2.0 ("Introduction"). Representative treatment systems and associated methods, are described under heading 3.0 ("Representative Treatment Systems and Associated Methods") with reference to FIGS. 1-3. Representative clinical data generated from the use of Applicant's treatment systems and methods disclosed herein are described under heading 4.0 ("Representative Clinical Data") with reference to FIG. 4-5C. The foregoing headings are provided for organizational purposes only. Features defined and/or described above under any of the foregoing headings may be combined with and/or applied to features described under any of the other headings, in accordance with embodiments of the present technology.

2.0 Definitions

As used herein, the terms "high frequency" and "HF" refer to a frequency of from about 1.2 kHz to about 100 kHz, or from about 1.5 kHz to about 100 kHz, or from about 2 kHz to about 50 kHz, or from about 3 kHz to about 20 kHz, or from about 3 kHz to about 15 kHz, or from about 5 kHz to about 15 kHz, or from about 3 kHz to about 10 kHz, or 1 kHz, 2 kHz, 3 kHz, 4 kHz, 5 kHz, 10 kHz, 15 kHz, 20 KHz, 50 kHz, or 100 kHz, unless otherwise stated. Unless otherwise stated, the term "about" refers to values within 10% of the stated value. As used herein, "low frequency" or "LF" refers to a frequency less than 1.2 kHz or less than 1 KHz.

As used herein, "peripheral neuropathy" refers to damage to or disease affecting one or more peripheral nerves or groups of peripheral nerves. Peripheral neuropathy may refer to nerve damage or disease in one nerve or area of the body (mononeuropathy), multiple nerves or multiple areas of the body (polyneuropathy), and/or in the same place on both sides of the body (symmetric neuropathy). Representative systems and methods in accordance with embodiments of the present technology are configured to treat all types of peripheral neuropathy, irrespective of whether it is inherited or acquired. Inherited causes include Charcot-Marie Tooth, Kennedy's disease (X-linked bilbospinal muscular atrophy), Van Allen's Syndrome (hereditary amyloid neuropathy), Refsum's disease, Tangier disease, and others. Causes of acquired peripheral neuropathy addressed by the systems and methods of the present technology include nerve compression, entrapment or laceration (e.g., crutches, ulnar neuropathy, thoracic outlet syndrome, meralgia paresthetica, Morton's metatarsalgia); metabolic (diabetes mellitus, hypothyroidism) and autoimmune disorders (lupus, rheumatoid arthritis, Guillain-Barre Syndrome, Miller Fisher Syndrome); kidney disease, liver disease, toxin-induced (alcohol, tobacco, asbestos, arsenic, lead, mercury); cancer (e.g., malignant lymphoma, lung cancer, etc.); viral or bacterial infections (HIV, Lyme disease, leprosy, poliomyelitis); medication-induced (e.g., chemotherapy, etc.); trauma; repetition (carpal tunnel syndrome, cubital tunnel syndrome); and vitamin deficiency (especially vitamin B).

As used herein, "treat" or "treatment" with reference to peripheral neuropathy includes preventing, ameliorating, suppressing, or alleviating one or more of the symptoms of abnormal sensory responses caused by peripheral neuropathy. In some cases, the treatment protocols of the present technology result in the reactivation of the nerve (e.g., restoring the ability of the nerve to depolarize and conduct signals).

As used herein, (the terms "sensory deficit," "sensory loss," "abnormal sensory response," "abnormal sensory function," etc. refer to all symptoms caused by disease and/or damage to the peripheral nerves (large and/or small fiber) of the somatosensory system, such as numbness, decreased responsiveness to light touch, pain, thermal sensation, and vibratory sensation, impaired joint position sense, impaired balance, and decreased muscle strength. The terms "somatosensory" refers generally to sensations (such as pressure, pain, or warmth) that can occur anywhere in the body, as opposed to a particular organ-specific sense, such as sight or smell. The foregoing terms also include "dysesthesia", an unpleasant and/or abnormal sense of touch, which in turn can include sensations of burning, wetness, itching, electric shock, and/or pins and needles, and which can affect any tissue, including but not limited to the mouth, skin, scalp and/or legs. When addressing or treating somatosensory dysfunction using high-frequency therapy signals in accordance with the present technology, the therapy signals may well have an effect on the patient's perception of pain—but in a different manner than that associated with existing techniques for treating chronic pain via high frequency signals. In particular, existing high frequency therapy signal regimens for addressing chronic pain are generally designed to reduce or eliminate pain (e.g., chronic, neuropathic pain). By contrast, when high frequency therapy signals are administered in accordance with the present technology to address or treat somatosensory dysfunction, they may operate to improve, restore or at least partly restore the patient's ability to detect and/or perceive pain. Now, if the patient also suffers from chronic pain, the high frequency therapy signal can be administered in a manner that also addresses (reduces) chronic pain, in addition to addressing somatosensory deficits.

3.0 Representative Treatment Systems and Associated Methods

Figure 1:
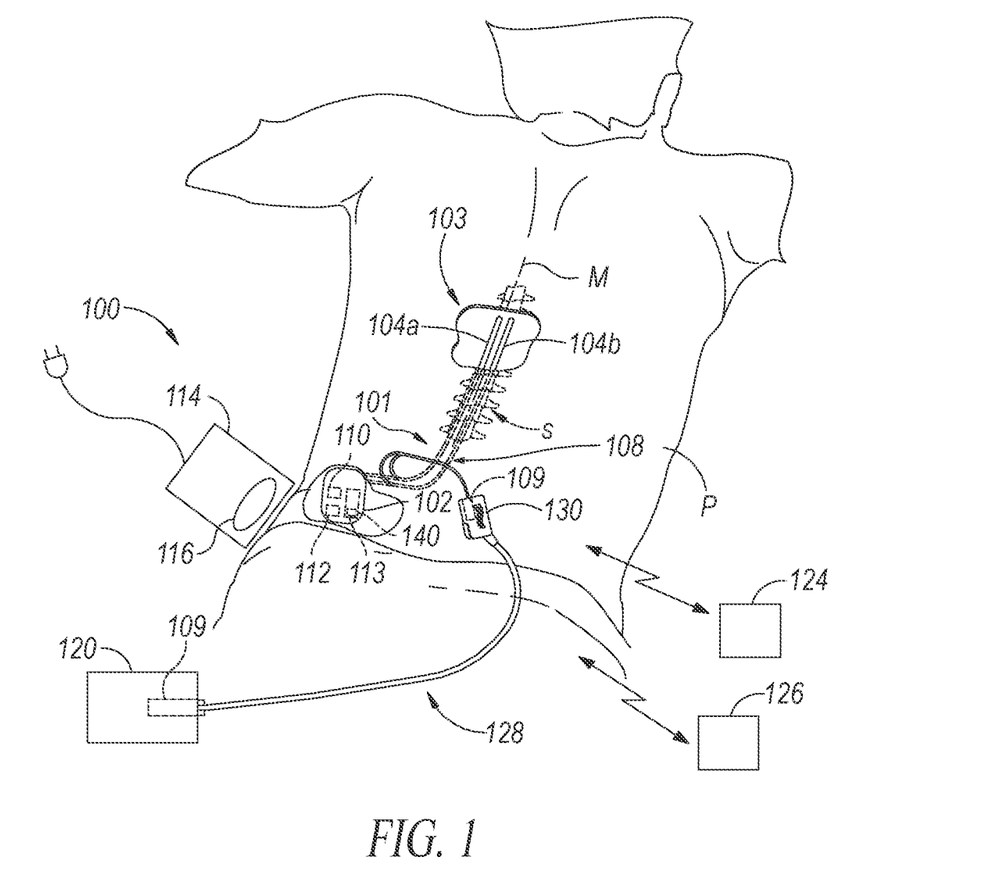
FIG. 1 is a partially schematic illustration of an implantable spinal cord modulation system positioned at the spine to deliver therapeutic signals in accordance with embodiments of the present technology.

FIG. 1 schematically illustrates a representative treatment system 100 for treating peripheral neuropathy and/or other sensory deficits, positioned relative to the general anatomy of a patient's spinal column S. The treatment system 100 can include a signal delivery system 101 having a signal generator 102 (e.g., a pulse generator) and a signal delivery device 103 comprising one or more signal delivery elements 104 (referred to individually as first and second signal delivery elements 104a, 104b, respectively). The signal generator 102 can be connected directly to the signal delivery element(s) 104, or it can be coupled to the signal delivery element(s) 104 via a signal link 108 (e.g., an extension). In some embodiments, the signal generator 102 may be implanted subcutaneously within a patient P. As shown in FIG. 1, the signal delivery element(s) 104 is configured to be positioned at or proximate to the spinal cord to apply a high frequency electrical signal to the spinal cord (e.g., to the white matter and/or glial cells of the spinal cord). Without being bound by theory, it is believed that glial cells are present in large concentrations within both white and grey matter, and that high frequency modulation at or proximate to the white and grey matter can affect electrically deficient glial cells. However, the therapies described herein may provide effective treatment via other mechanisms of action.

In representative embodiments, the signal delivery device 103 includes the first and second signal delivery elements 104a, 104b, each of which comprises a flexible, isodiametric lead or lead body that carries features or structures, for delivering an electrical signal to the treatment site after implantation. As used herein, the terms "lead" and "lead body" include any of a number of suitable substrates and/or support members that carry structures, for providing therapy signals to the patient. For example, the lead body can include one or more electrodes or electrical contacts that direct electrical signals into the patient's tissue, such as to directly affect a cellular membrane. In some embodiments, the signal delivery device 103 and/or signal delivery elements 104 can include devices other than a lead body (e.g., a paddle) that also direct electrical signals and/or other types of signals to the patient. Additionally, although FIG. 1 shows an embodiment utilizing two signal delivery elements 104, in some embodiments the signal delivery system 101 and/or signal delivery device 103 can include more or fewer signal delivery elements (e.g., one signal delivery element, 104 three signal delivery elements 104, four signal delivery elements 104, etc.), each configured to apply electrical signals at different locations and/or coordinate signal delivery to deliver a combined signal to the same (or generally the same) anatomical location.

As shown in FIG. 1, the first signal delivery element 104a can be implanted on one side of the spinal cord midline M, and the second signal delivery element 104b can be implanted on the other side of the spinal cord midline M. For example, the first and second signal delivery elements 104a, 104b shown in FIG. 1 may be positioned just off the spinal cord midline M (e.g., about 1 mm offset) in opposing lateral directions so that the first and second signal delivery elements 104a, 104 are spaced apart from each other by about 2 mm. In some embodiments, the first and second signal delivery elements 104a, 104b may be implanted at a vertebral level ranging from, for example, about T8 to about T12. In some embodiments, one or more signal delivery devices can be implanted at other vertebral levels, depending, for example, on the specific indication for which the patient is being treated.

The signal generator 102 can transmit signals (e.g., electrical therapy signals) to the signal delivery element 104 that up-regulate (e.g., stimulate or excite) and/or down-regulate (e.g., block or suppress) target nerves (e.g., local vagal nerves). As used herein, and unless otherwise noted, to "modulate," "stimulate," or provide "modulation" or "stimulation" to the target nerves refers generally to having either type of the foregoing effects on the target nerves. The signal generator 102 can include a machine-readable (e.g., computer-readable) medium containing instructions for generating and transmitting suitable therapy signals. The signal generator 102 and/or other elements of the treatment system 100 can include one or more processors 110, memories 112 and/or input/output devices 140. Accordingly, the process of providing electrical signals, detecting physiological parameters of the patient, adjusting the modulation signal, and/or executing other associated functions can be performed by computer-executable instructions contained by computer-readable media located at the signal generator 102 and/or other system components. The signal generator 102 can include multiple portions, elements, and/or subsystems (e.g., for directing signals in accordance with multiple signal delivery parameters) housed in a single housing, as shown in FIG. 1, or in multiple housings.

The signal delivery system 101 can include one or more sensing elements 113 for detecting one or more physiological parameters of the patient before, during, and/or after the application of electrical therapy signals. In some embodiments, one or more of the sensing elements 113 can be carried by the signal generator 102, the signal delivery element 104, and/or other implanted components of the system 101. In some embodiments, the sensing element 113 can be an extracorporeal or implantable device separate from the signal generator 102 and/or signal delivery element 104. Representative sensing elements 113 include one or more of: a subcutaneous sensor, a temperature sensor, an impedance sensor, a chemical sensor, a biosensor, an electrochemical sensor, a hemodynamic sensor, an optical sensor and/or other suitable sensing devices. Physiological parameters detected by the sensing element(s) 113 include neurotransmitter concentration, local impedance, current, and/or voltage levels, and/or any correlates and/or derivatives of the foregoing parameters (e.g., raw data values, including voltages and/or other directly measured values).

The signal generator 102 can also receive and respond to one or more input signals received from one or more sources. The input signals can direct or influence the manner in which the therapy and/or process instructions are selected, executed, updated, and/or otherwise performed. The input signals can be received from one or more sensors (input devices, 140 (e.g., the sensor 113) shown schematically in FIG. 1 for purposes of illustration) that are carried by the signal generator 102 and/or distributed outside the signal generator 102 (e.g., at other patient locations) while still communicating with the signal generator 102. The sensor 113 and/or other input devices 140 can provide inputs that depend on or reflect patient state (e.g., patient position, patient posture, and/or patient activity level), and/or inputs that are patient-independent (e.g., time). Still further details are included in U.S. Pat. No. 8,355,797, which is incorporated herein by reference.

In some embodiments, the signal generator 102 can obtain power to generate the therapy signals from an external power source 114. The external power source 114 can transmit power to the implanted signal generator 102 using electromagnetic induction (e.g., RF signals). For example, the external power source 114 can include an external coil 116 that communicates with a corresponding internal coil (not shown) within the implantable signal generator 102. The external power source 114 can be portable for ease of use.

In some embodiments, the signal generator 102 can obtain the power to generate therapy signals from an internal power source, in addition to or in lieu of the external power source 114. For example, the implanted signal generator 102 can include a non-rechargeable battery or a rechargeable battery to provide such power. When the internal power source includes a rechargeable battery, the external power source 114 can be used to recharge the battery. The external power source 114 can in turn be recharged from a suitable power source (e.g., conventional wall power).

During at least some procedures, an external generator 120 (e.g., a trial stimulator or modulator) can be coupled to the signal delivery element 104 during an initial procedure, prior to implanting the signal generator 102. For example, a practitioner (e.g., a physician and/or a company representative) can use the external generator 120 to provide therapy signals and vary the modulation parameters provided to the signal delivery elements 104 in real time, and select optimal or particularly efficacious parameters. These parameters can include the location from which the electrical signals are emitted, as well as the characteristics of the electrical signals provided to the signal delivery elements 104. In some embodiments, input is collected via the external generator 120 and can be used by the clinician to help determine what parameters to vary. In a typical process, the practitioner uses a cable assembly 128 to temporarily connect the external generator 120 to the signal delivery element 104. The practitioner can test the efficacy of the signal delivery elements 104 in an initial position. The practitioner can then disconnect the cable assembly 128 (e.g., at a connector 130), reposition the signal delivery elements 104, and reapply the electrical signal. This process can be performed iteratively until the practitioner obtains the desired signal parameters and/or position for the signal delivery element 104. Optionally, the practitioner can move the partially implanted signal delivery element 104 without disconnecting the cable assembly 128. Furthermore, in some embodiments, the iterative process of repositioning the signal delivery elements 104 and/or varying the therapy parameters may not be performed. Instead, the practitioner can place signal delivery element(s) 104 at an approximate anatomical location, and then select which electrodes or contacts deliver the therapy signal, as a way of varying the location to which the therapy signal is directed, without repositioning the signal delivery element(s).

After the signal delivery elements 104 are implanted, the patient P can receive therapy via signals generated by the external generator 120, generally for a limited period of time. During this time, the patient wears the cable assembly 128 and the external generator outside the body. Assuming the trial therapy is effective or shows the promise of being effective, the practitioner then replaces the external generator 120 with the implanted signal generator 102, and programs the signal generator 102 with therapy programs selected based on the experience gained during the trial period. Optionally, the practitioner can also replace the signal delivery elements 104. The signal delivery parameters provided by the signal generator 102 can still be updated after the signal generator 102 is implanted, via a wireless physician's programmer 124 (e.g., a physician's remote) and/or a wireless patient programmer 126 (e.g., a patient remote). Generally, the patient P has control over fewer parameters than does the practitioner. For example, the capability of the patient programmer 126 may be limited to starting and/or stopping the signal generator 102, and/or adjusting the signal amplitude. The patient programmer 126 may be configured to accept pain relief input as well as other variables, such as medication use.

The signal generator 102, the lead extension, the external programmer 120 and/or the connector 130 can each include a receiving element 109. Accordingly, the receiving elements 109 can be implantable elements (implantable within the patient), or the receiving elements 109 can be integral with an external patient treatment element, device or component (e.g., the external generator 120 and/or the connector 130). The receiving elements 109 can be configured to facilitate a simple coupling and decoupling procedure between the signal delivery elements 104, the lead extension, the signal generator 102, the external generator 120, and/or the connector 130. The receiving elements 109 can be at least generally similar in structure and function to those described in U.S. Patent Application Publication No. 2011/0071593.

Figure 2:
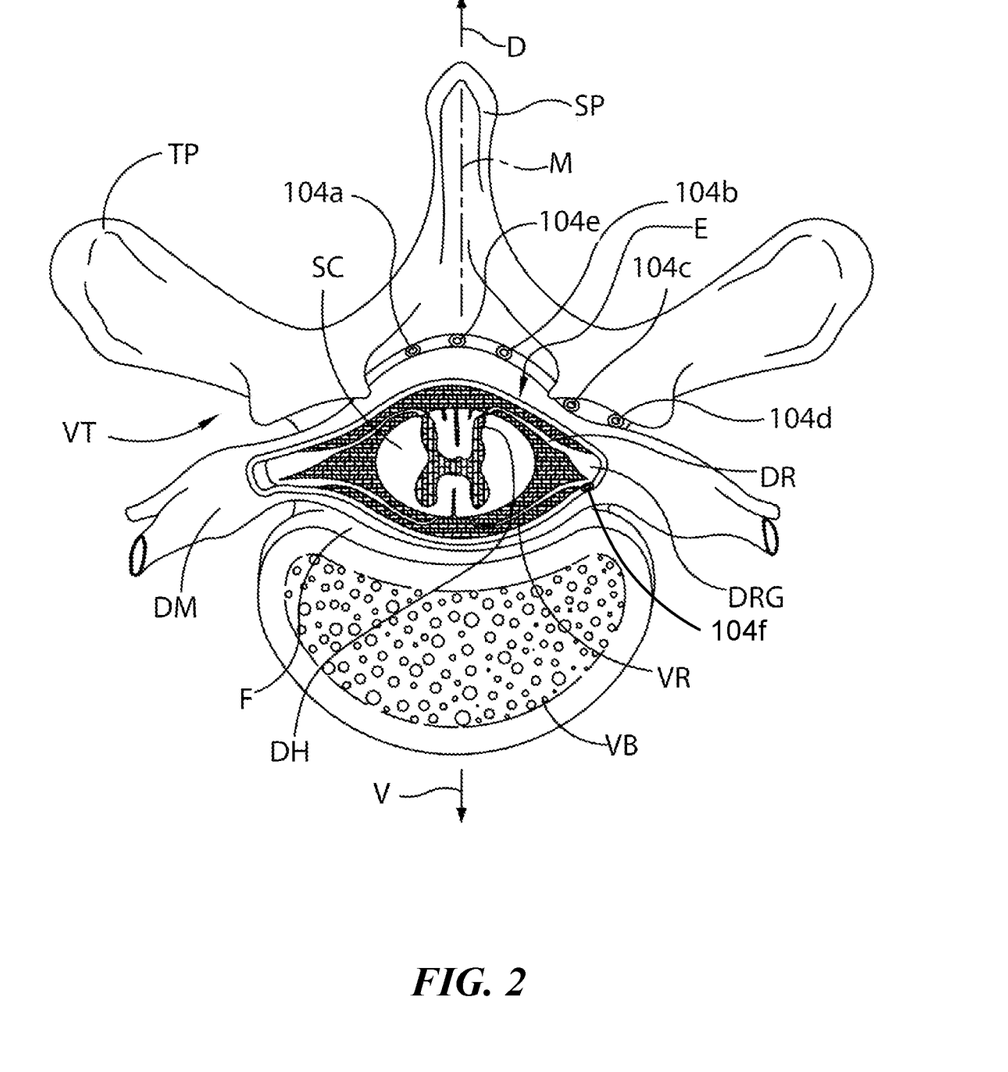
FIGS. 2-3 are partially schematic, cross-sectional illustrations of a patient's spine, illustrating representative locations for implanted lead bodies in accordance with embodiments of the present technology.
Figure 3:
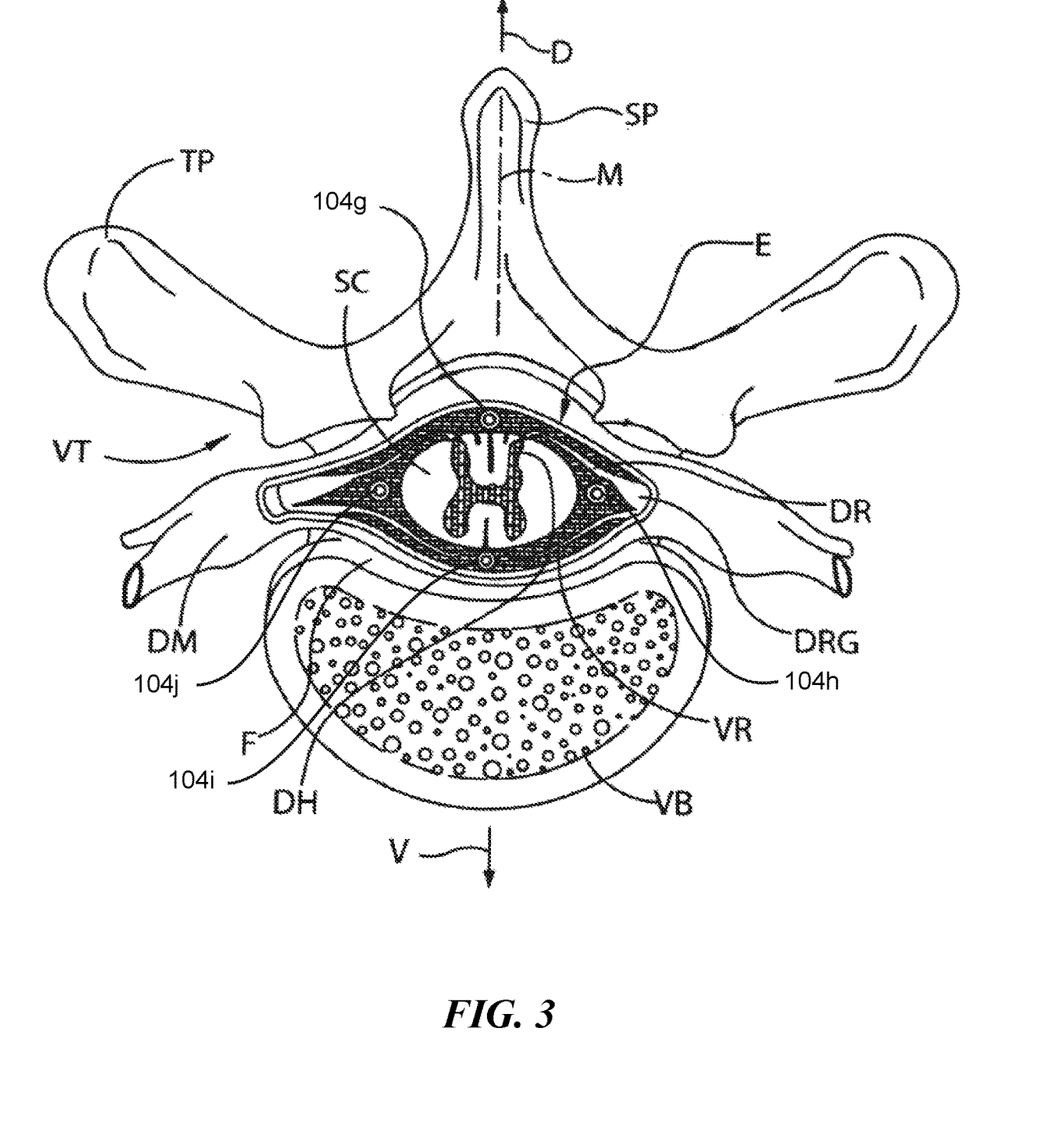

FIG. 2 is a cross-sectional illustration of a spinal cord SC and an adjacent vertebra VT (based generally on information from Crossman and Neary, "Neuroanatomy," 1995 (published by Churchill Livingstone)), along with multiple signal delivery elements 104 (shown as signal delivery elements 104a-104f) implanted at representative locations. For purposes of illustration, multiple signal delivery elements 104 are shown in FIG. 2 implanted in a single patient. In actual use, any given patient will likely receive fewer than all the signal delivery elements 104 shown in FIG. 2.

As shown in FIG. 2, the spinal cord SC is situated within a vertebral foramen F, between a ventrally located ventral body VB and a dorsally located transverse process TP and spinous process SP. Arrows V and D identify the ventral and dorsal directions, respectively. The spinal cord SC itself is located within the dura mater DM, which also surrounds portions of the nerves exiting the spinal cord SC, including the ventral roots VR, dorsal roots DR and dorsal root ganglia DRG. The dorsal roots DR enter the spinal cord SC at the dorsal root entry zone E, and communicate with dorsal horn neurons located at the dorsal horn DH. In one embodiment, the first and second signal delivery elements 104a, 104b are positioned just off the spinal cord midline M (e.g., about 1 mm offset) in opposing lateral directions so that the two signal delivery elements 104a, 104b are spaced apart from each other by about 2 mm. In other embodiments, a lead or pairs of leads can be positioned at other epidural locations, e.g., toward the outer edge of the dorsal root entry zone E as shown by a third signal delivery element 104c, or at the dorsal root ganglia DRG, as shown by a fourth signal delivery element 104d, or approximately at the spinal cord midline M, as shown by a fifth signal delivery element 104e, or near the ventral roots, as shown by a sixth signal delivery element 104f. In some embodiments, the leads are positioned near the exit of the ventral roots may be advantageous to modify ventral motor pools located in the gray matter. For example, modification of these ventral motor pools may treat spasticity, motor disorders and/or other disorders arising from the ventral motor pools.

In some embodiments, it may be advantageous to position one or more signal delivery elements 104 within the dura mater DM to target neural tissue and one or more glial cells present in the gray and white matter of the spinal cord SC. For example, as shown in the cross-sectional view of a spinal cord SC in FIG. 3, in some embodiments a seventh signal delivery element 104g and an eighth signal delivery element 104i are positioned along the spinal cord midline M on the dorsal and ventral sides of the spinal cord SC, respectively. In some embodiments, one or more signal delivery elements 104 can be positioned at other locations. For example, in some embodiments a ninth signal delivery element 104h and a tenth signal delivery element 104j are positioned off the spinal cord midline M on opposing lateral sides of the spinal cord SC. High frequency signals applied to the tenth signal delivery element 104j may be especially effective at reducing sympathetic outflow. In some embodiments, high frequency signals applied to the tenth signal delivery element 104j may treat heart failure, hypertension, complex regional pain syndrome, peripheral vascular disease, and other diseases where elevated sympathetic tone is implicated. In some embodiments, one or more signal delivery elements 104 may be positioned in other suitable locations within the subdural space. Additionally, in some embodiments, a physician may position one or more signal delivery elements in the epidural space and one or more signal delivery elements in the subdural space. More generally any one of the foregoing signal delivery elements may be used alone or in combination with any other signal delivery element(s) 104, depending upon the patent indication(s).

4.0 Representative Clinical Data

Figure 4:
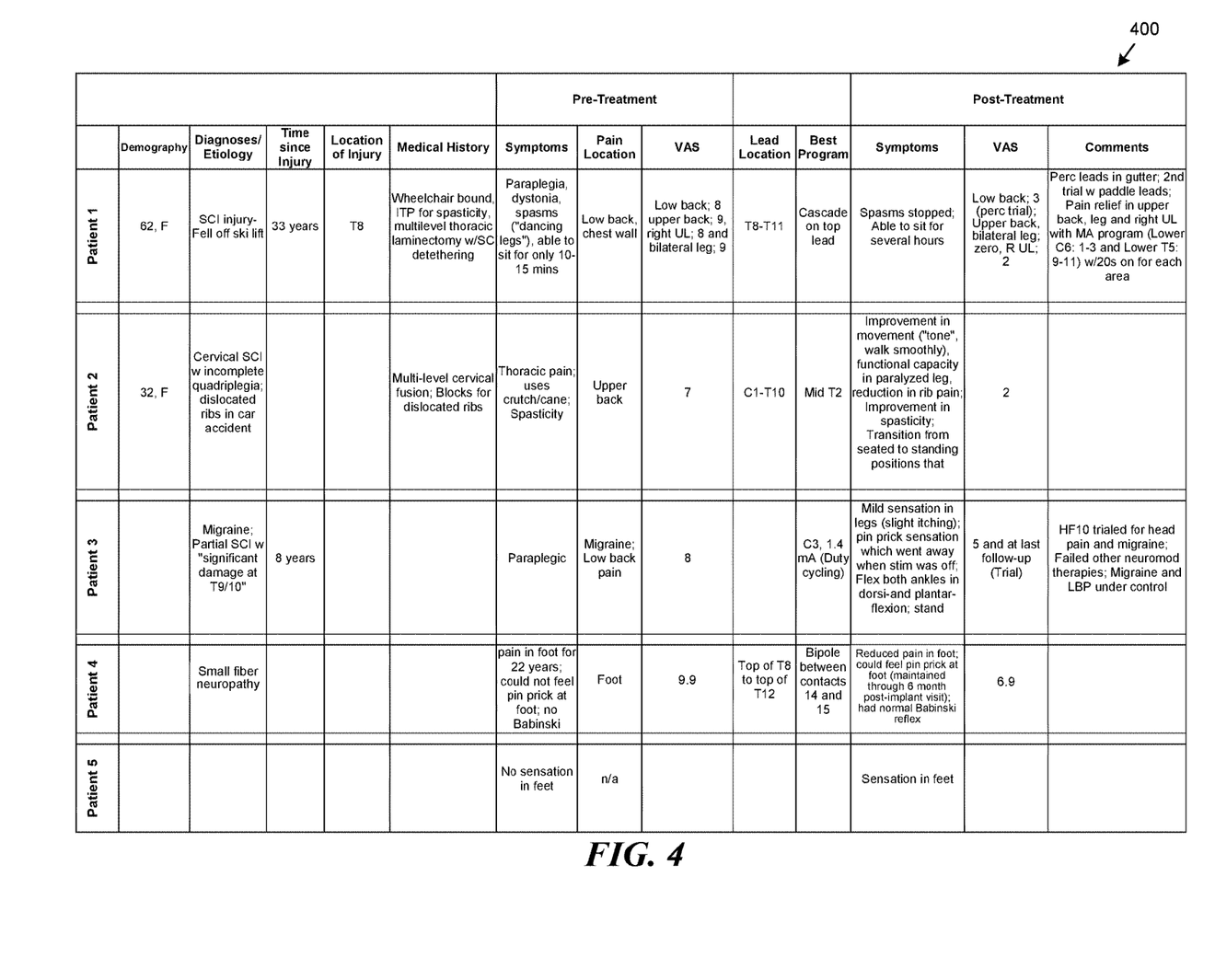
FIG. 4 is a table showing selected clinical data gathered from Applicant's clinical study showing treatment of sensory deficit with high frequency spinal cord stimulation, in accordance with embodiments of the present technology.

FIG. 4 is a table 400 of selected clinical data gathered during Applicant's clinical study in which patients were implanted with one or more signal delivery elements in accordance with the devices, systems, and methods described in under heading 3.0 above. In particular, patients received electrical therapy signals at a frequency of 10 KHz, a pulse width of 30 microseconds, and an amplitude that ranged from about 0.5 mA to about 6 mA.

TABLE 400

| includes the following acronyms/abbreviations: |
| --- |
| SCI - spinal cord injury |
| ITP - Intrathecal pump |
| UL - Upper Limb |
| R - Right |
| SC - Spinal cord |
| MA program - Multi-area program |
| LBP - Low back pain |

As shown in the first row of the table 400, Patient 1 suffered from upper and lower back pain caused by a spinal cord injury at the eighth thoracic vertebrae. Patient 1 was paraplegic and presented with dystonia, spasms ("dancing legs"), and low back and chest wall pain. Before treatment, Patient 1 was able to sit comfortably for only 10-15 minutes. Based on Patient 1's pain location (lower and upper back), the lead electrodes were placed at or between the eighth and the eleventh thoracic vertebrae (T8-T11). After treatment, Patient 1's spasms were gone, and Patient 1 was able to sit for several hours.

As shown in the second row of table 400, Patient 2 suffered from thoracic pain caused by a cervical spinal cord injury. Patient 2 presented with a paralyzed leg, and spasticity. Before treatment, Patient 2 required a crutch for walking. Based on Patient 2's pain location (thoracic), the lead electrodes were placed at or near the vertical midpoint of the second thoracic vertebrae (T2). After treatment, Patient 2 had improved movement (i.e., improved "tone", and was able to walk smoothly), renewed functional capacity in the paralyzed leg, a reduction in thoracic pain, improvement in spasticity, and was able to transition from seated to standing positions that caused spasms or tone problems before treatment.

As shown in the third row of table 400, Patient 3 suffered from low back pain caused by a partial spinal cord injury with significant damage at the ninth and tenth thoracic vertebra (T9-T10). Patient 3 was paraplegic and also presented with migraines. Based on Patient 3's pain indications, the lead electrodes were placed at the third cervical vertebrae (C3). Patient 3's migraine and low back pain were successfully treated. After treatment, Patient 3's ability to sense slight itching was restored, and Patient 3 was able to sense pinpricks in the legs as long as the high frequency stimulation was being delivered. Patient 3 was also able to flex both ankles in dorsi- and plantar-flexion, bend his legs at both knees, stand up and bear weight with support, and had spontaneous return of erectile function.

As shown in the fourth row of table 400, Patient 4 presented with foot pain from small fiber neuropathy (peripheral neuropathy) and could not sense a pin-prick sensation in that foot. Patient 4 presented with Babinski reflex, severe and constant muscle spasms in the back, constant burning sensation at the skin, and stabbing pain in the low- and mid-back. Based on Patient 4's pain indication, the lead electrodes were placed to span from the superior aspect of the eighth thoracic vertebrae (T8) to the superior aspect of the twelfth thoracic vertebrae (T12). After treatment, Patient 4 experienced restored pin-prick sensations in the foot, the Babinski reflex disappeared and the patient experienced reduced pain in the foot.

As shown in the fifth row of table 400, Patient 5 presented with no pin prick sensation. After a trial period, Patient 5 had restored pin prick sensation in the feet. Sensation was maintained at follow-up visits. Ten additional patients (not represented in table 400) also presented with no pin prick sensation, and also had their pinprick sensation restored following treatment in accordance with the foregoing parameters (frequency of 10 kHz, a pulse width of 30 microseconds, and an amplitude that ranged from about 0.5 mA to about 6 mA). These cases, as well as others discussed herein, are representative of patients recovering pain-based sensory responses via a high frequency electrical therapy.

An additional patient, not represented in table 400, was a paraplegic SCI patient, with a lesion at T11 and with neuropathic lower back pain. His T10-L2 vertebral bodies were fused as a result of injury. Following several failed (more conservative) therapies, he received a high frequency therapy regimen in accordance with the foregoing parameters via a single lead positioned epidurally between the T10-L1 vertebral bodies. In general, leads for high frequency therapy are placed at T8-T11 for back pain, but in this case, the lead could not be advanced (in a rostral direction) past mid-T10. The patient had a dural puncture during the procedure and the resulting headache prevented accurate reporting of pain scores for the first two days of the trial period. However, by the third day, the patient reported significant back pain relief. At the end of the seven day trial period, the patient reported 80% pain relief and was able to voluntarily move his leg for the first time in 15 years. Sensation to touch and pin prick were restored from the L1-S1 dermatomes. His neurological status improved from spastic paralysis at baseline to non-spastic weakness. In addition, for the last three days of the trial, the patient had regained micturition control and had stopped self-catheterizing.

The electrical therapy treatment methods of the present technology may be used with other therapies (e.g., conventional therapies) for peripheral neuropathy treatment. Such therapies include, but not limited to: corticosteroids; IV immunoglobulins; plasma exchange or plasmapheresis; immunosuppressive agents; surgery; mechanical aids; avoiding toxins including alcohol; aldose reductase inhibitors; fish oil; gamma-linolenic acid; gangliosides; lipoic acid; myoinositol; nerve growth factor; protein kinase C inhibitors; pyridoxine; ruboxistaurin mesylate; thiamine; vitamin B12; pain relievers including codeine; anti-seizure medications including gabapentin, topiramate, pregabalin, carbamazepine, and phenytoin; topical anesthetics such as lidocaine; tricyclic antidepressant medications such as amitriptyline and nortriptyline; selective serotonin and norepinephrine reuptake inhibitors such as duloxetine; and mexiletine. The agents may also include, for example, dopamine uptake inhibitors, monoamine oxidase inhibitors, norepinephrine uptake inhibitors, dopamine agonists, acetocholinesterase inhibitors, catechol O-methyltransferase inhibitors, anticholinergic agents, antioxidants, as well as synaptic and axonal enhancing medications. Additionally, it has been observed that HF therapy can reduce the need for supplemental medications. For example, in a randomized controlled trial of HF therapy for low back and leg pain, concomitant morphine-equivalent medication use and dosage were significantly reduced. Thus, in the context of the present technology, those agents used as primary, supplemental, or adjuvant treatments can be reduced, bringing the benefit of both reduced side-effects and patient compliance burden, when HF therapy is successfully applied.

Further Clinical Results

The following sections described further clinical results obtained by treating patients with therapy signals at frequencies in the range of 1.5 kHz to 100 kHz.

(a) Peripheral Polyneuropathy

Figure 5A:
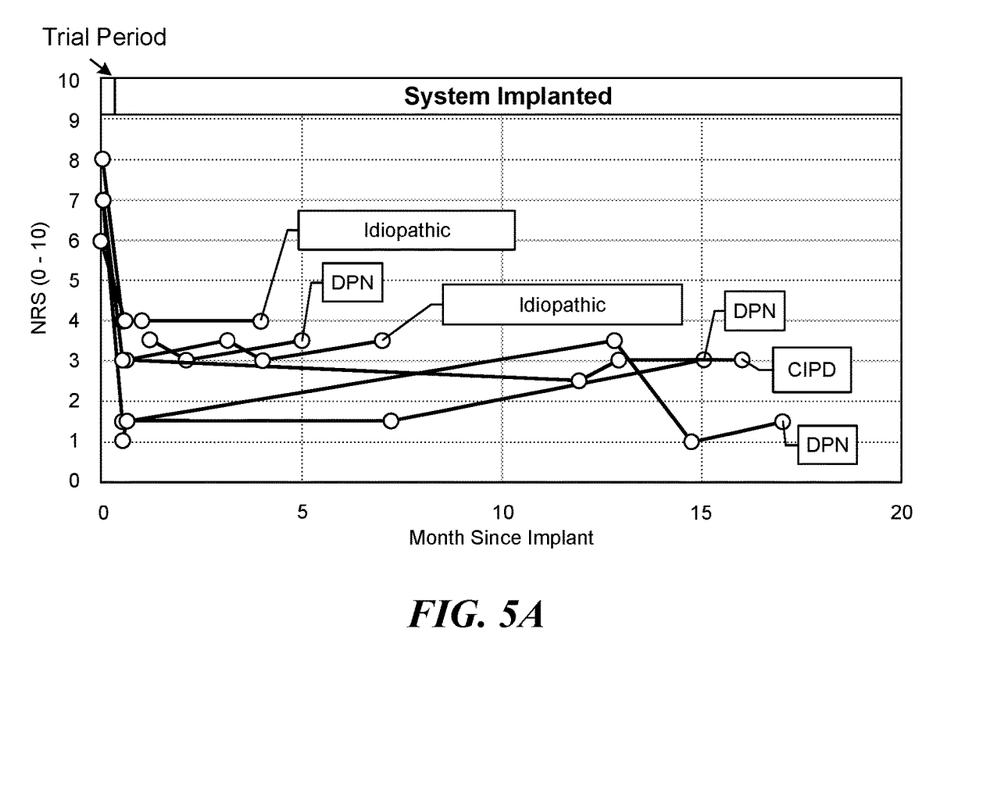
FIGS. 5A-5C illustrate clinical results for patients treated for peripheral polyneuropathy with high frequency stimulation in accordance with embodiments of the present technology.
Figure 5B:
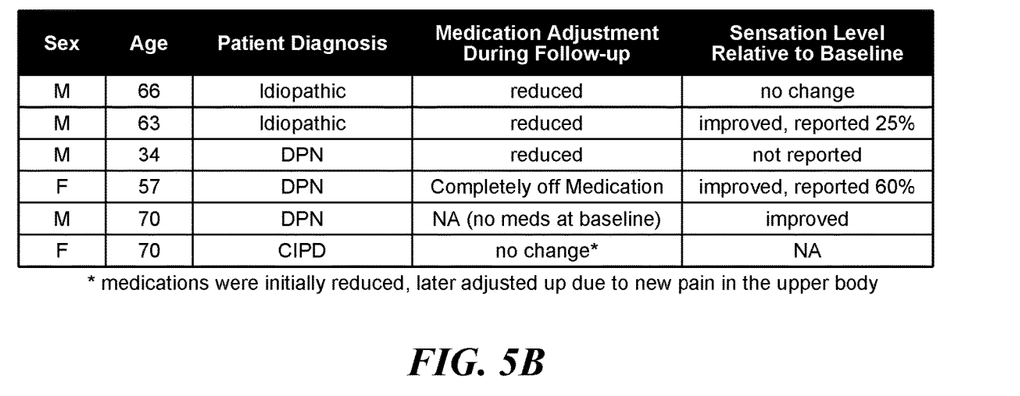
Figure 5C:
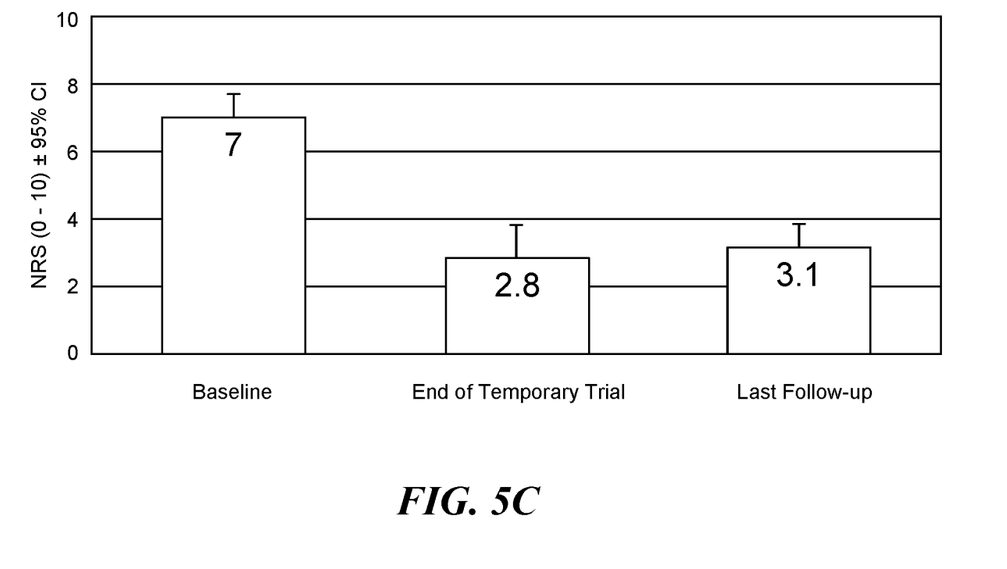

FIGS. 5A-5C illustrate data obtained from six peripheral polyneuropathy patients, all presenting with bilateral lower extremity pain. Each of the patients was treated with a therapy signal at 10 kHz, applied to the patient at the T8-T11 vertebral level. The signal had a pulse width of 30 microseconds, and an amplitude that varied from patient to patient. As shown in FIG. 5A, three patients were diagnosed with diabetic peripheral neuropathy, two patients with idiopathic peripheral neuropathy, and one patient with chronic inflammatory demyelinating polyneuropathy. Five of the six patients experienced at least a 50% reduction in pain during an approximately one week trial period, and all were implanted with a pulse generator and signal delivery device.

As shown in FIG. 5B, four of the five patients who received medication prior to receiving treatment via the 10 KHz therapy signal had their medication reduced or eliminated. As is also shown in FIG. 5B, several of the patients also reported an improvement in sensation level relative to baseline.

FIG. 5C illustrates the pain scores of the patients at baseline, at the end of the temporary trial, and as of a subsequent follow-up (10.7 months, plus or minus 6 months). These data indicate that the patients received a significant reduction in pain, which was sustained over a significant period after the trial period.

Anecdotally, an additional diabetic patient (not included in the data shown in FIGS. 5A-5C) suffered a significant amount of pain in his lower legs, which were ulcerated. He was near to receiving an amputation of his leg, prior to receiving electrical signal therapy at 10 KHz via an implanted stimulation device in accordance with the foregoing parameters. After stimulation for a period of two months, the patient's pain was reduced, the patient's wounds were healing, the color returned to the patient's legs, and the patient was walking, whereas previously the patient had been in a wheelchair.

(b) Post-Stroke Pain

In still a further example, patients were treated for central post-stroke pain (CPSP). CPSP refers to chronic neuropathic pain resulting from lesions of the central somatosensory nervous system, particularly the spinothalamocortical pathway. The prevalence of CPSP is 1-12% in stroke patients, and symptom onset usually occurs within six months. Most patients complain of burning, allodynia, and hyperalgesia. CPSP is typically pharmacoresistant, and therapeutic options for refractory cases are limited.

An 85-year-old male with a prior history of hypertension, pre-diabetes, and stroke presented for management of right lower extremity (RLE) pain. One year earlier, he had presented with a new left-sided weakness. Following a stroke diagnosis, he underwent intensive rehabilitation and had near complete resolution of left hemibody weakness. However, six months later, he began to experience new RLE pain. Workup for re-stroke was negative. The patient's pain was constant and burning, with an average intensity of 8 on a numerical rating scale of 0-10 for pain assessment, and associated with allodynia and hyperalgesia. He received no benefit from amitriptyline, physical therapy or a right lumbar sympathetic block.

The patient received spinal cord stimulation at 10 kHz, with a signal delivery device spanning the T8-T11 vertebral bodies. The patient received a successful trial and then underwent permanent implantation. At an 8-week follow-up, he reported greater than 80% pain relief, with an average pain score of 2 and significant improvement in his quality of life. Based at least upon this patient's outcome, it is believed that stimulation in accordance with the foregoing parameters can prove effective for medically refractory CPSP.

(c) Foot Drop

In another example, two patients presented with both chronic low back pain, and bilateral foot drop following complications from prior spinal surgeries. Patient 1, a 62-year-old woman, experienced persistent foot drop for 13 years, ambulating with aides. Electromyogram (EMG) tests revealed mild sensorimotor axonal polyneuropathy, with demyelinating features. The patient was affected by chronic neurogenic deficits affecting vertebral levels L4-L5 and S1 bilaterally, with active denervation affecting the L5 root on the right side. The patient had been prescribed with analgesics for control of pain at a level of 8 out of 10 on the numerical rating scale, which induced unpleasant side effects.

Patient 2 was a 45-year-old male who suffered from acute paraplegia complications following spinal surgery. His neurological deficit gradually improved, but his back pain and bilateral lower extremity weakness remained, with this right side worse, resulting in an ankle-foot orthosis. Arachnoiditis was evident at the L4-L5 level, with significant clumping of the nerve roots at this level. The patient received strong analgesics for his back pain, which was at a level of 5-8/10 on the numerical rating scale.

After receiving stimulation at 10 KHz during a trial, both patients proceeded to a permanent implant at a vertebral level of T8-T11. By three months post-implant, both patients no longer required orthotics, and began weaning opioids. At six months, Patient 1's foot drop had completely resolved, with a return of sensation and no pain. At nine months, Patient 1 had weaned off opioids completely, reporting significant improvements in function without aides, and was able to drive a car. Patient 2 no longer used opioids at six months post-implant, and reported almost complete resolution of his foot drop. In addition, Patient 2 reported an average pain score of one on a scale of ten, improved walking, and the ability to ride a bicycle.

It is expected that dorsally positioned electrodes can provide the foregoing motor benefits. For example, dorsal white matter tracts feed into spinal grey matter circuits to inhibit/facilitate reflex and motor coordination. In pathologic states, or in the absence of descending control, these circuits may become dysfunctional, e.g., spastic, tonic, and/or dis-coordinated. HF therapy can 'normalize' these circuits via grey matter and/or glial effects, to restore patient function and activities of daily living.

(d) Dysesthesia

In still further example, several patients suffering from dysesthesia were treated with spinal cord stimulation at a frequency of 10 kHz, a pulse width of 30 microseconds, and a current amplitude that varied from patient to patient. Prior to treatment, the patients were diagnosed with peripheral polyneuropathy and/or painful diabetic neuropathy. Some patients experienced the inability to feel the bottoms of their feet, which created balance and gait issues, and some patients experienced foot numbness and tingling. After 6-7 days of receiving therapy at 10 KHz, the foot numbness and tingling disappeared, and the patients experienced an improvement in gait.

The foregoing gait and sensory improvements can be particularly significant for patients suffering from diabetes, because when such patients can walk, they are better able to control their blood sugar. Patients are also better able to avoid falls and fractures, which are additional issues associated with diabetic patients.

Based on the foregoing, it is expected that stimulation in accordance with the foregoing parameters can be used to address lower limb pain, foot and ankle pain, other types of focal, neuropathic pain, and/or dysesthesia. These results are expected to be achieved with spinal cord stimulation delivered at 10 KHz or other high frequency values, to the dorsal column of the patient's spinal cord. This is contrary to conventional techniques, which may require that stimulation be applied to the dorsal root ganglion.

In addition, based on the foregoing results, stimulation in accordance with the parameters disclosed herein can produce benefits in addition to, or in lieu of, pain reduction. Such benefits involve restoration of sensory and/or motor functions.

Further Indications

The discussion above describes representative therapies in the context of treatment for spinal cord injury, peripheral neuropathy and other indications. In some embodiments, the therapy can be administered to patients with peripheral polyneuropathy indications. More generally, the therapy can be applied to patients with other indications, other indications that are associated with sensory loss, and/or motor deficits. As an example, in at least some cases, the observed sensory improvement is correlated (e.g., other indications directly or indirectly) with motor improvement. Accordingly, the foregoing techniques can be used to facilitate sensory and/or motor function recovery. In particular, at least one patient (Patient 2 described above with reference to FIG. 4) experienced a reduction in spasticity, as well as other motor-related improvements, in addition to a reduction in pain.

It is expected that, in at least some embodiments, the foregoing therapies can be used to address sensory deficit, and/or motor deficit, and/or spinal cord injury, in combination with treating pain. In some embodiments, the foregoing therapies can be used to address sensory deficit, and/or motor deficit, and/or spinal cord injury, independent of whether or not the therapy is also used to treat pain. In at least some embodiments, the target location of the therapy signal may be different, depending on whether the therapy is used to address pain, or one or more of a sensory deficit, motor deficit, or spinal cord injury. For example, in at least some cases, it was found that therapy delivered to treat segmental pain also produced an improvement in sensory response, but at a location rostral or caudal to the segmental pain indication.

It is also believed that sensory deficit can be reversed when treating polyneuropathy, without moving the therapy treatment site, and that foot pain can be addressed with a more generalized treatment location (e.g., T8-T12), as opposed to a specific location (such as the DRG at L5 or S1). More generally, it is believed that the therapy can be applied to the spinal cord instead of the DRG (which is where at least some conventional low frequency treatments are applied). Advantages of applying the therapy signal to the spinal cord rather than the DRG include (a) a lower incidence of adverse events/safety concerns, and/or (b) a broader electric field spread that may have additional pain and/or other benefits, whereas DRG stimulation is typically very focal. In addition, implanting the signal delivery device at the spinal cord may be simpler and easier to "standardize" than implanting the signal delivery device at the DRG.

Several embodiments of the present technology were described above in the context of therapy signals applied to the patient's spinal cord region. In other embodiments, the therapy signal may be applied to other locations, e.g., peripheral locations.

Without being bound by theory, it is possible that treating motor and sensory deficits may result from different mechanisms of action. For example, it may be that hyperpolarization of the lamina I/II interneurons explains the resolution of spastic/dystonic (motor) symptoms (e.g., caused by a barrage of spontaneous firing), and the therapies described above hyperpolarize those cells resulting a reduced/normalized neuronal activity level. Because sensory deficit may be due to lack of input from neurons, the ability to address sensory deficit as well as motor symptoms via the same therapy signal may be an indication that different mechanisms of action are responsible for each result. For example, the beneficial effect on motor symptoms may result from a reversal of inhibition or hyperpolarization. Alternatively, the normalization of the sensory input may be the cause of a reduced motor dysfunction. In other words, the sensorimotor reflex may be returned to normal when the sensory neuron returns to normal.

Representative Signal Delivery Parameters

The therapy signals described above may be delivered in accordance with several suitable signal delivery parameters. For example, the signal frequency may be from about 1.2 kHz to about 100 kHz, or from about 1.5 kHz to about 100 kHz, or from about 2 kHz to about 50 kHz, or from about 3 kHz to about 20 kHz, or from about 3 kHz to about 15 kHz, or from about 5 kHz to about 15 kHz, or from about 3 kHz to about 10 KHz, or 1 kHz, 2 kHz, 3 kHz, 4 kHz, 5 kHz, 10 kHz, 15 kHz, 20 kHz, 50 KHz, or 100 kHz. In particular embodiments, representative current amplitudes for the therapy signal are from 0.1 mA to 20 mA, or 0.5 mA to 10 mA, or 0.5 mA to 7 mA, or 0.5 mA to 5 mA. Representative pulse widths range from about 10 to about 333 microseconds, about 10 to about 166 microseconds, about 25 to about 166 microseconds, about 20 to about 100 microseconds, about 30 to about 100 microseconds, about 30 to about 40 microseconds, about 10 to about 50 microseconds, about 20 to about 40 microseconds, about 25 to about 35 microseconds, about 30 to about 35 microseconds, and about 30 microseconds. Duty cycles can range from about 10% to about 100%, and in a particular duty cycle, signals are delivered for 20 seconds and interrupted for 2 minutes (an approximate 14% duty cycle). In other embodiments, these parameters can have other suitable values. Other suitable parameters and other therapy features are disclosed in the following materials, each of which is incorporated by reference: U.S. Patent Application Publication No. US2009/0204173; U.S. Patent Application Publication No. US2014/0296936; and U.S. Patent Application Publication No. US2010/0274314.

From the foregoing, it will be appreciated that specific embodiments of the disclosed technology have been described herein for purposes of illustration, but that various modifications may be made without deviating from the technology. Certain aspects of the technology described in the context of particular embodiments may be combined or eliminated in other embodiments. Further, while advantages associated with certain embodiments of the disclosed technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein. The following examples provide further representative embodiments of the presently disclosed technology.

As used herein, the phrase "and/or," as in "A and/or B" refers to A alone, B alone, and A and B. To the extent any materials incorporated by reference herein conflict with the present disclosure, the present disclosure controls.

We claim:

1. A method of treating a patient having sensation loss, via spinal cord stimulation, comprising:
in response to the patient having sensation loss, programming a signal generator to deliver a non-paresthesia producing electrical signal having a frequency in a frequency range of 5 kHz to 16 kHz to the patient's spinal cord via at least one implanted signal delivery element,
wherein the non-paresthesia producing electrical signal at least partially restores the sensation that was lost, and wherein the sensation was lost in association with diabetic neuropathy.

2. The method of claim 1 wherein the signal generator is implantable, the at least one implanted signal delivery element is positioned in the patient's thoracic vertebral region between T8 and T12, and the non-paresthesia producing electrical signal has (a) a pulse width in a pulse width range of 10 microseconds to 333 microseconds, and (b) an amplitude in an amplitude range of 0.5 milliamps to 10 milliamps.

3. The method of claim 1 wherein the non-paresthesia producing electrical signal has a frequency of 10 KHz.

4. The method of claim 1 wherein the non-paresthesia producing electrical signal has a pulse width in a pulse width range of 10 microseconds to 333 microseconds.

5. The method of claim 1 wherein the non-paresthesia producing electrical signal has a pulse width in a pulse width range of 25 microseconds to 35 microseconds.

6. The method of claim 1 wherein the non-paresthesia producing electrical signal has an amplitude in an amplitude range of 0.5 milliamps to 10 milliamps.

7. The method of claim 1 wherein the at least one implanted signal delivery element is positioned in the patient's thoracic vertebral region.

8. The method of claim 7 wherein the at least one implanted signal delivery element is positioned in the patient's thoracic vertebral region between T8 and T12, inclusive.

9. The method of claim 1 wherein the at least one implanted signal delivery element is positioned in the patient's epidural space.

10. The method of claim 1 wherein the sensation loss is in the patient's foot or leg, and wherein the non-paresthesia producing electrical signal at least partially restores the sensation that was lost in the patient's foot or leg.

11. The method of claim 1 wherein the non-paresthesia producing electrical signal at least partially alleviates extremity pain associated with the diabetic neuropathy in addition to restoring the sensation.

12. The method of claim 1 wherein the sensation lost in association with the diabetic neuropathy includes sensation loss caused by diabetes.

13. A method of treating a patient having a loss of sensation, via spinal cord stimulation, comprising:
   in response to patient having sensation loss associated with diabetic neuropathy, programming a signal generator to deliver, via at least one implanted signal delivery element, a non-paresthesia producing electrical signal having a frequency in a frequency range of 5 kHz to 15 kHz to the patient's spinal cord to at least partially restore the sensation that was lost in association with diabetic neuropathy.

14. The method of claim 13 wherein the signal generator is implantable, the at least one implanted signal delivery element is positioned in the patient's thoracic vertebral region between T8 and T12, and the non-paresthesia producing electrical signal has (a) a pulse width in a pulse width range of 10 microseconds to 333 microseconds, and (b) an amplitude in an amplitude range of 0.5 milliamps to 10 milliamps.

15. The method of claim 13 wherein the non-paresthesia producing electrical signal has a frequency of 10 KHz.

16. The method of claim 13 wherein the non-paresthesia producing electrical signal has (a) a pulse width in a pulse width range of 10 microseconds to 333 microseconds, and (b) an amplitude in an amplitude range of 0.5 milliamps to 10 milliamps.

17. The method of claim 13 wherein the non-paresthesia producing electrical signal has (a) a pulse width in a pulse width range of 25 microseconds to 35 microseconds, and (b) an amplitude in an amplitude range of 0.5 milliamps to 10 milliamps.

18. The method of claim 13 wherein the at least one implanted signal delivery element is positioned in the patient's thoracic vertebral region between T8 and T12, inclusive.

19. The method of claim 13 wherein the non-paresthesia producing electrical signal at least partially eliminates sensations of tingling, pins-and-needles, and/or electric shock associated with the diabetic neuropathy.

20. The method of claim 13 wherein the sensation loss is in the patient's foot or leg, and wherein the non-paresthesia producing electrical signal at least partially restores the sensation that was lost in the patient's foot or leg.

21. The method of claim 13 wherein the non-paresthesia producing electrical signal at least partially alleviates extremity pain associated with the diabetic neuropathy in addition to restoring the sensation.

22. The method of claim 13 wherein the sensation lost in association with the diabetic neuropathy includes sensation loss caused by diabetes.

23. A method of treating a patient having sensation loss, via spinal cord stimulation, comprising:
   in response to the patient having sensation loss associated with diabetic neuropathy, directing an electrical signal having a frequency in a frequency range of 5 kHz jo 15 khz to the patient's spinal cord region via an implanted signal delivery element,
   wherein the electrical signal at least partially restores the sensation that was lost in association with diabetic neuropathy without causing paresthesia in the patient.

24. The method of claim 23 wherein the electrical signal has (a) a pulse width in a pulse width range of 10 microseconds to 333 microseconds, and (b) an amplitude in an amplitude range of 0.5 milliamps to 10 milliamps.

25. The method of claim 23 wherein the electrical signal at least partially alleviates sensations of tingling, pins-and-needles, and/or electric shock associated with the diabetic neuropathy in addition to restoring the sensation.

* * * * *